(12) United States Patent
Nielsen et al.

(10) Patent No.: US 9,877,874 B2
(45) Date of Patent: Jan. 30, 2018

(54) ADHESIVE DRESSING

(71) Applicant: Coloplast A/S, Humlebaek (DK)

(72) Inventors: Anders Christian Nielsen, Bagsvaerd (DK); Tune Bjarke Bonné, Fredensborg (DK); Mehrdad Jafari, Copenhagen (DK)

(73) Assignee: Coloplast A/S, Humlebaek (DK)

( * ) Notice: Subject to any disclaimer, the term of this patent is extended or adjusted under 35 U.S.C. 154(b) by 202 days.

(21) Appl. No.: 14/646,152

(22) PCT Filed: Nov. 20, 2013

(86) PCT No.: PCT/DK2013/050393
§ 371 (c)(1),
(2) Date: May 20, 2015

(87) PCT Pub. No.: WO2014/079459
PCT Pub. Date: May 30, 2014

(65) Prior Publication Data
US 2016/0045376 A1 Feb. 18, 2016

(30) Foreign Application Priority Data

Nov. 21, 2012 (DK) ................................ 2012 70724
Mar. 13, 2013 (DK) ................................ 2013 70150

(51) Int. Cl.
*A61F 13/00* (2006.01)
*A61F 13/02* (2006.01)

(52) U.S. Cl.
CPC ........ *A61F 13/025* (2013.01); *A61F 13/0236* (2013.01); *A61F 13/0253* (2013.01); *A61F 13/0289* (2013.01)

(58) Field of Classification Search
CPC .... A61F 13/02; A61F 13/0253; A61F 13/025; A61F 13/036; A61F 13/0236; A61F 13/0287; A61F 13/0289
USPC ............................................................ 602/55
See application file for complete search history.

(56) References Cited

U.S. PATENT DOCUMENTS

| | | | | |
|---|---|---|---|---|
| 1,707,515 A | * | 4/1929 | Evans | A61F 13/02 428/121 |
| 2,310,082 A | * | 2/1943 | Holbrooke | A61F 13/0273 602/55 |
| 2,349,709 A | * | 5/1944 | Evans | A61F 13/0283 427/208.6 |

(Continued)

FOREIGN PATENT DOCUMENTS

DE 102010053610 A1 6/2012
FR 2609889 A1 7/1988
(Continued)

*Primary Examiner* — Kim M Lewis
(74) *Attorney, Agent, or Firm* — Coloplast Corp., Coloplast A/S; Nick Baumann

(57) ABSTRACT

An adhesive dressing for application to the skin or a wound, the dressing comprising a backing layer having a skin facing surface and a non-skin facing surface, the skin facing surface being provided with substantially parallel adhesive lanes arranged with a distance in between such that the adhesive lanes are spaced from each other's by a portion of uncoated backing layer. The configuration of the dressing provides improved flexibility and permeability of the dressing.

12 Claims, 6 Drawing Sheets

(56) References Cited

U.S. PATENT DOCUMENTS

| | | | | |
|---|---|---|---|---|
| 2,399,545 A | * | 4/1946 | Davis | C09J 7/04 |
| | | | | 602/55 |
| 3,811,438 A | * | 5/1974 | Economou | A61F 13/0203 |
| | | | | 602/55 |
| 5,578,152 A | | 11/1996 | Goulait et al. | |
| 7,902,420 B2 | * | 3/2011 | Kase | A61F 13/023 |
| | | | | 206/440 |
| 2007/0292491 A1 | * | 12/2007 | Hansen | A61K 8/0208 |
| | | | | 424/448 |

FOREIGN PATENT DOCUMENTS

| | | |
|---|---|---|
| JP | H06184502 | 7/1994 |
| JP | 2006075648 A2 | 3/2006 |
| JP | 2006-087488 | 4/2006 |
| JP | 2006167129 A2 | 6/2006 |
| JP | 2007512055 T2 | 5/2007 |
| JP | 2007215578 A2 | 8/2007 |
| WO | 8905619 A1 | 6/1989 |
| WO | WO 2005051333 A1 * | 6/2005 |
| WO | 2007/121744 | 11/2007 |

* cited by examiner

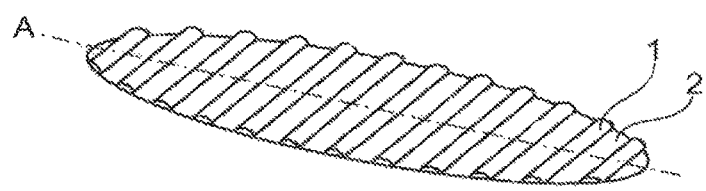
Fig. 1
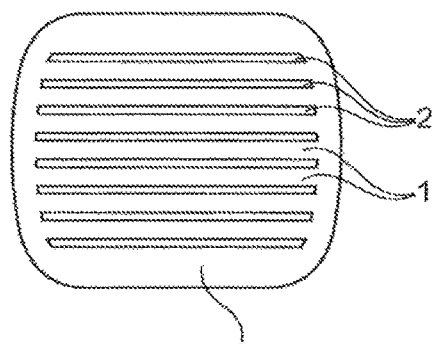
Fig. 2
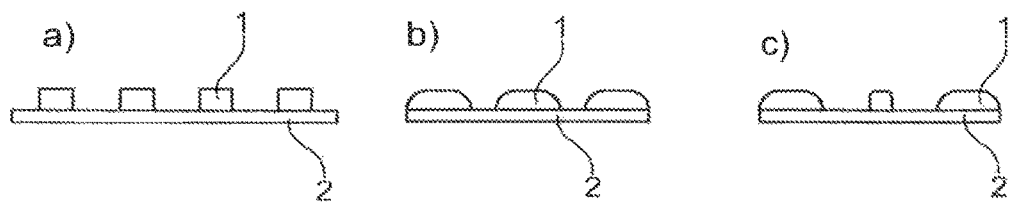
Fig. 3
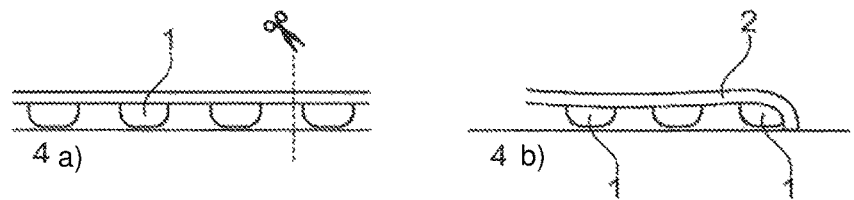
Fig. 4a
Fig. 4b

ADHESIVE DRESSING

The invention relates to adhesive wound dressings for application to intact or damaged skin, especially at protruding body parts or otherwise curved application sites on the body.

BACKGROUND

Wound dressings are typically flat structures with limited flexibility. This may give rise to challenges when the dressing has to be applied to a protruding body part such as fingertips, knuckles, elbows or knees. The dressing may easily wrinkle at the edges, and discomfort due to the limited flexibility may occur. Prior art solutions involves using softer adhesives, thereby often compromising the absorption properties of the dressing, thinner dressings, compromising cushioning effect of the dressing, as well as tailor made shapes for the particular application or pattern of indentations in the adhesive.

Limited moisture handling may give rise to maceration of the skin. To overcome maceration, CMC based hydrocolloid particles or other absorbing materials may be compounded into the adhesive matrix. Another way to overcome such limitations with respect to moisture handling is inclusion of various patterns that could limit material thickness in certain areas, hence improving moisture throughput of the entire dressing. Both solutions, however, also have some limitations themselves; a hydrocolloid dressing will delay water uptake due to the nature of such compounded systems, where availability of the water handling particles might be buried deep in the hydrophobic matrix. Pattern structure may solve some of such issues; however manufacturing might be complicated and time consuming due to discontinuous step process.

SUMMARY OF THE INVENTION

One object of the invention is to provide a highly flexible dressing without compromising the absorbent properties.

An object of the invention is to facilitate inspection of the wound without removing the dressing.

Yet an object of the invention is to provide a dressing construction where the adhesive force of the dressing may be adjusted, using the same adhesive but altering the configuration of the dressing.

Yet another object is to provide an adhesive dressing that is capable of handling exudates through evaporation.

BRIEF DESCRIPTION OF THE DRAWING

FIG. 1 illustrates an embodiment of the solution seen in perspective,

FIG. 2 discloses another embodiment of the invention seen from above,

FIG. 3a-c shows different embodiments of the invention in cross-section and

FIG. 4a-b shows a cross section of an embodiment being cut.

DETAILED DESCRIPTION OF THE INVENTION

Figure 5:
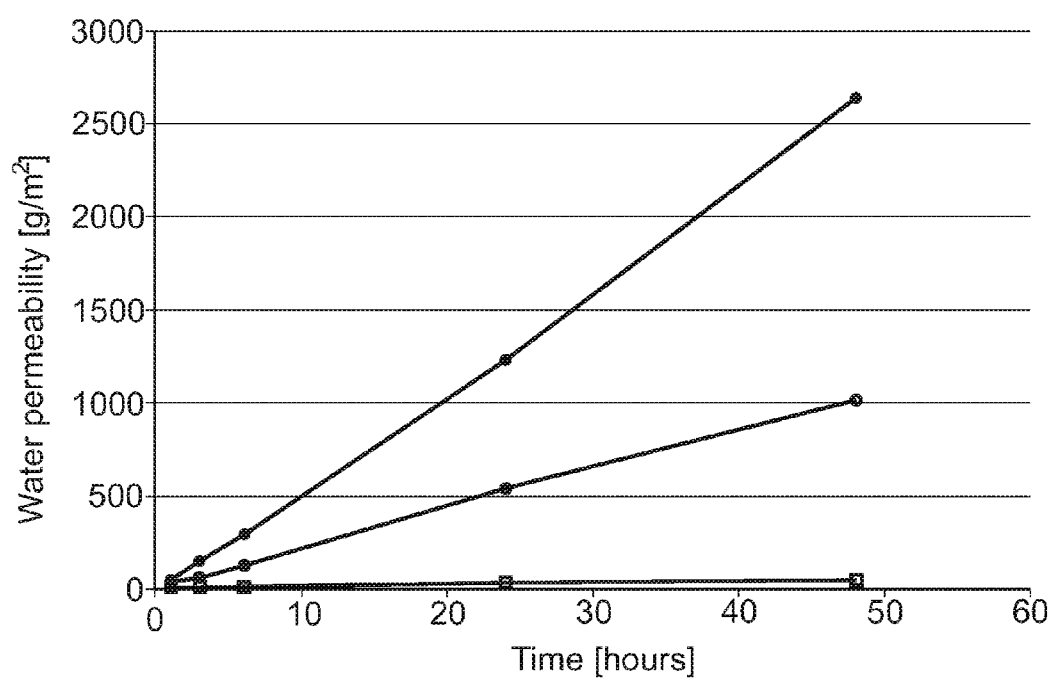
FIG. 5 shows a water permeability test.

In a first aspect, the invention relates to an adhesive dressing for application to the skin or a wound, the dressing comprising a backing layer having a skin facing surface and a non-skin facing surface, the skin facing surface being provided with substantially parallel adhesive lanes arranged with a distance in between such that the adhesive lanes are spaced from each other by a portion of uncoated backing layer wherein the thickness of the adhesive lanes is 0.25-0.9 mm.

By providing adhesive in narrow parallel lanes on a backing layer, improved flexibility and moisture handling of the dressing is achieved. Such dressings are suitable for application to damaged or intact skin, such as to blisters, wounds, eczema or exposed skin portions that need protection. The adhesive facilitates good adhesion and moisture handling, and the non-adhesive portions between the adhesive portions provides the dressing with a high flexibility, rendering it possible to apply the dressing to protruding body parts with no or less wrinkles in the dressing and reducing the stress to the skin.

Furthermore, by providing the adhesive in lanes, the adhesive force of the dressing can be adjusted and tailor made for the desired purpose, without changing the adhesive composition. Thus, easy removal of the dressing may be facilitated.

It has surprisingly been found, that using parallel lanes as illustrated above, provides a high level of flexibility in the final dressing. Especially, when used on areas where it is difficult to apply dressings, such as fingertips, elbows etc. When using a traditional flat adhesive patch, even the thin ones, folds may occur, compromising long term adhesion, visual appearance and comfort of the dressing.

By substantially parallel is meant that the distance between neighboring lanes is substantially invariable across the dressing from one edge to the other so that the distance between neighboring lanes at the most varies 0.05 mm.

The thickness is defined as the direction across the dressing from the skin facing surface to the non-skin facing surface.

The thickness of the adhesive lanes may be 0.1-1 mm, such as 0.2-0.9 mm, 0.2-0.8 mm, 0.25-0.9 mm, 0.25-0.8 mm, 0.3-8 mm or even 0.3-0.7 mm. The lanes may be substantially rectangular in cross-section or they may have a more rounded configuration. The thickness of the adhesive lanes as defined herein is measured at the thickest point, typically in the middle of the lane.

The thickness of the adhesive lanes may provide the dressing with a cushioning effect. Furthermore, if the adhesive is absorbent, the absorption capacity of the dressing may increase with an increase in thickness of the adhesive layer.

The width of the lanes may be 0.5-6 mm, such as 1-5 mm, such as 2-5 mm, 2.5-5 mm or even 3-4 mm. The width is measured from edge to edge of an individual lane. All the lanes of the dressing may have the same width or they may have different widths.

The width of the lanes may be at least 50%, such as at least 75% or even at least 100% of the thickness of the lanes.

The width of the lanes may be at least 50%, such as 75% or even 100% wider than the width of the space between the adhesive lanes.

Between the lanes there is a space volume not being covered by adhesive. The width of this space between the lanes may be the same or smaller than the width of the adhesive lanes. The width of the space volume may be 0.5-6 mm, such as 1-5 mm, such as 2-5 mm, 2.5-5 mm or even 3-4 mm. The space volume of between the lanes may be empty in the sense that the volume being only filled by air.

The pattern of lanes may be symmetric in the sense that the width of the adhesive lanes is the same as the width of the non-adhesive space volume between the lanes.

The dressing facilitates better moisture handling due to uncoated volumes that can hold liquid, as well as because of the increased adhesive area exposed due to the height of such volumes.

The parallel adhesive lanes are substantially linear or the lanes may be curved, for example wave-shaped or in a zigzag pattern.

The lanes may extend from edge to edge of the dressing. The lanes may be across the longest dimension of the dressing or the may be in the longitudinal direction of the dressing. In one embodiment, the lanes may be on a slant, for example defining an angle of approximately 45 degrees to a central axis, symmetric of the dressing.

The dressing may comprise a continuous adhesive edge portion. Such edge portion may be advantageous in order to control exudates from seeping out of the dressing via the non-adhesive space volumes.

The dressing may be in the form of an elongated tape that can be cut off or ripped off in suitable pieces. The lanes may be substantially perpendicular to the length direction of the tape, rendering it possible to cut the tape along a non-adhesive portion. When cut, the excessive backing layer will sweep down and thereby a thick, exposed adhesive edge is avoided as would elsewhere occur when cutting in adhesive dressings.

The adhesive may be a hydrocolloid adhesive, being capable of handling moisture from a blister or wound. The dressing may be provided with the same adhesive all over, or the dressing may comprise two or more kinds of adhesive, arranged in different lanes.

In one embodiment, the dressing may comprise one or more lanes of a non-adhesive character, such as an ointment, créme or the like.

One or more of the adhesive lanes may comprise an active ingredient, such as agents for promoting wound healing, reducing pain or infection. Examples of such ingredients may be silver compounds or ibuprofen.

The backing layer may be water impervious vapour permeable, thereby facilitating high permeability, but yet protecting the wound from contamination and dirt. In one embodiment, the backing layer is a polyurethane film.

The backing layer may be transparent or translucent, enabling that the wound may be inspected through the dressing without loosening the adhesive and removing the dressing. The non-adhesive interspaces between the adhesive lanes may be transparent or translucent to facilitate inspection.

In another aspect, the invention relates to a method of producing an adhesive dressing comprising the steps of providing a support layer, disposing adhesive from at least one nozzle over a comb to one surface of the support layer, thereby creating a pattern of substantially parallel adhesive lanes separated by strips of uncoated support layer.

The support layer may be a release layer, either being a temporary transport layer during the production process, or it may be used as a release liner in the final product. The release layer has non-stick properties, e.g. in the form of a coating, in order to facilitate easy release of the adhesive from the release layer. Subsequently, a backing layer may be laminated to the adhesive lanes.

The support layer may be the backing layer of the final dressing, thus, the adhesive may be coated directly to the backing layer.

The backing layer with the adhesive lanes may subsequently be cut into individual dressings and optionally be bevelled at the edge portion.

The height of the adhesive lanes enables the backing layer to stick to the side portions of such lanes, hence positioning the backing layer closer to the surface, forming an overall tighter bond between dressing and skin/wound. This increases the ability of the dressing to adhere to complicated and protruding surfaces that elsewhere would have been difficult with more flat or patterned designs.

This dressing solution is easy to manufacture, as the coating process is easy and fast, and the subsequent moulding into dressings is simple and well known as well. The moulding is further simplified by the fact that the space volumes work as reservoirs for the excess material to be moved around during a bevelling process, thus putting less stress on the materials in the dressing.

DETAILED DESCRIPTION OF THE DRAWING

The invention will now be described in further detail with reference to the figures.

FIG. 1 shows an embodiment of the dressing in perspective, the dressing comprising a backing layer (2) being provided with discrete adhesive lanes (1) extending from edge to edge of the dressing and being substantially perpendicular to the symmetric length axis (A) of the dressing.

FIG. 2 shows an embodiment wherein the dressing is provided with a continuous adhesive border (3). The central portion of the dressing is provided with discrete curved lanes (1) of adhesive.

FIG. 3a shows an embodiment wherein the cross sectional shape of the adhesive lanes (1) is substantially rectangular. In FIG. 3b the cross section of the lanes (1) is rounded and FIG. 3c shows an embodiment wherein the adhesive lanes (1) have different width.

FIG. 4 shows an embodiment of the invention, for example the embodiment shown in FIG. 1, being cut. By cutting the dressing along a space volume, the end piece of the backing layer may sweep down around the neighbouring adhesive lane, thereby avoiding an exposed thick adhesive border that may stick to the clothes and/or absorb moisture.

EXPERIMENTAL

Water Permeability (MVTR)

The water permeability over time of three samples was determined.

Sample 1: backing layer without adhesive coating,

Sample 2: backing layer coated on one side with substantially parallel adhesive lanes, separated by adhesive free zones, Sample 3: backing layer coated with a continuously layer of adhesive.

The backing layer of the three samples was in the form of a 30 μm thick PU-film. In Sample 2 and 3 the adhesive was bevelled at the edge portion and the samples had a surface area of 8.6 $cm^2$.

Sample 1 was in the form of a backing layer of a size of 020 mm (3.14 $cm^2$).

The adhesive lanes of Sample 2 had a width of 5 mm and were separated by an adhesive free lane of a width of 2.5 mm.

The thickness of the adhesive layer of Sample 2 and 3 were 0.35 mm.

The water permeability over time was determined and the result appears from FIG. 5, where filled circles represent Sample 1, empty circles represent Sample 2 and empty squares represent Sample 3. As can be seen, the permeability of the dressing according to the invention was significantly higher than the permeability of a full-coated adhesive backing layer but lower than the uncoated backing layer.

The water permeability (MVTR) was determined by the international standard ASTM 96, the inverted cup method. 0.9% NaCl solution was used as liquid and the test was performed at 37° C. and 15% RH.

Elongation

The elongation of a sample dressing was measured using a sample size of 25×100 mm. The sample was mounted in a tensile strength apparatus and stretched 100% of its original length (100 mm to 200 mm) using a speed of 500 mm/min. The applied force at 100% was recorded. The tests were done with the adhesive lanes of the dressing being respectively perpendicular and parallel to the pull direction.

Elongation Perpendicular to Lanes

Table 1 shows the force needed to extend the samples 100% for different adhesive lane widths. All the samples had an adhesive thickness of 0.5 mm and the backing layer was in the form of a 30 μm thick PU-film.

TABLE 1

| Distance [mm]: | Force [N]: |
| --- | --- |
| Backing layer (no adhesive) | 3.29 |
| 0 (full adhesive coating) | 5.45 |
| 1 | 3.91 |
| 3 | 4.17 |
| 5 | 3.85 |

As can be seen from Table 1, the force needed to extend the dressing was lower when the adhesive was coated in lanes, facilitating a more flexible and less rigid dressing.

Elongation Parallel to Lanes

Table 2 shows the force needed to extend the samples 100% for different widths of the adhesive lanes. All the samples had an adhesive thickness of 0.5 mm and the backing layer was in the form of a 30 μm thick PU-film.

TABLE 2

| Distance [mm]: | Force [N]: |
| --- | --- |
| 0 | 5.9 |
| 1 | 4.68 |
| 3 | 4.72 |
| 5 | 4.79 |

Again it can be seen, that the force needed to extend the dressing was lower, when it is provided with adhesive lanes, though the impact was not as distinct as for the perpendicular lanes.

Geometry

Relations between the dimensions of the adhesive lanes and the space between the lanes were investigated.

If the dressing is to be provided with a continuous adhesive edge portion encircling a central part of the dressing, the dimensions of the adhesive lanes in the central part may be optimized. The dressing may be produced by providing a backing layer with adhesive lanes separated by portions without adhesive and applying heat and pressure to the edge portion, thereby facilitating the adhesive lanes at the edge portion to flow together to create a continuous adhesive edge portion. However, in order to do this, the thickness of the adhesive and distance between the lanes should be balanced; if the thickness of the adhesive is too low and at the same time the distance between the lanes are too high, then it may be difficult to close the edges to form a continuous edge portion. If the edges are open, wound exudates may leak out from the dressing as well as dirt may enter under the dressing and contaminate the skin/wound. On the other hand, if the thickness of the lanes is too high and/or the distance between them is too low, then the lanes may not be well defined as they will flow or stick together.

In order to determine the relationship between the geometry of the lanes and the ability to facilitate a closed edge portion, a number of adhesives samples were produced where the thickness and the distance between the lanes were varied. The samples were visually evaluated with regard to whether they were closed at the edges and at the same time had well defined lanes.

The samples comprised a 30 μm thick polyurethane backing layer coated on one surface with adhesive lanes as described below. The adhesive is a styrene-isoprene-styrene (SIS) adhesive and comprises 38% hydrocolloids in the form of carboxymethyl cellulose (CMC).

The results are shown in the Table 3 below. The adhesive lanes of the samples were symmetrical, meaning that the adhesive lanes had the same width as the width of the non-adhesive space between them.

TABLE 3

| | | Adhesive thickness | | |
| --- | --- | --- | --- | --- |
| | | 0.1 mm | 0.5 mm | 1.0 mm |
| Distance between lanes | 1 mm | 1 | OK | 2 |
| | 3 mm | 1 | OK | OK |
| | 5 mm | 1 | OK | OK |

1: Edges do not close
2: The lanes not defined properly, they flow together

In the following, FIGS. 6-10 describe the three situations shown in Table 3.

Edge Closed, Well Defined Lanes

Figure 6:
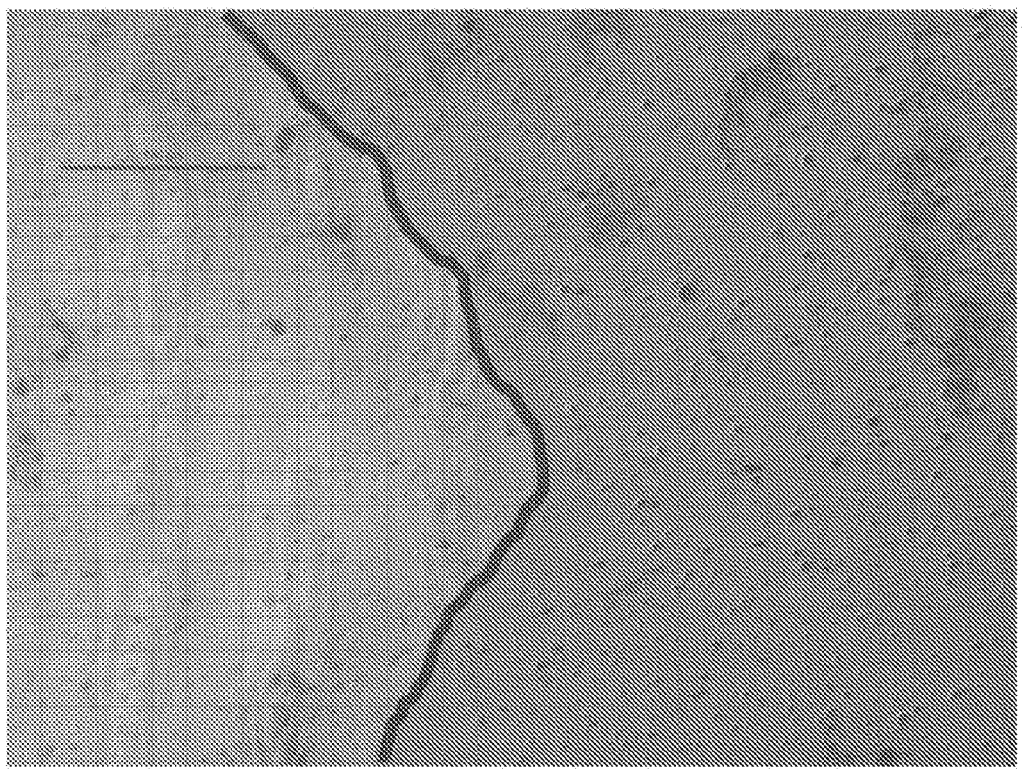
FIGS. 6-10 show results of a dimension test of the adhesive lanes.

The microscope picture in FIG. 6 shows a close-up of the edge portion where the edges were found closed correctly. The black line was drawn to show the transition between adhesive and no adhesive.

Figure 7:
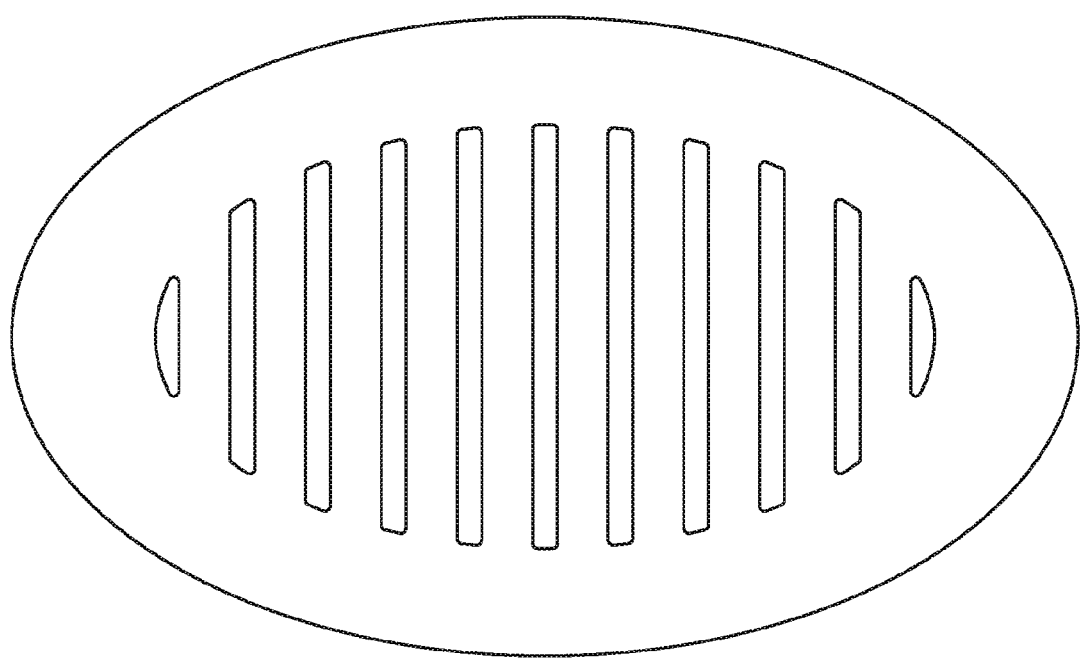

FIG. 7 shows the same dressing as in FIG. 6. The edge was closed, but the lanes are still well defined.

Open Edges

Figure 8:
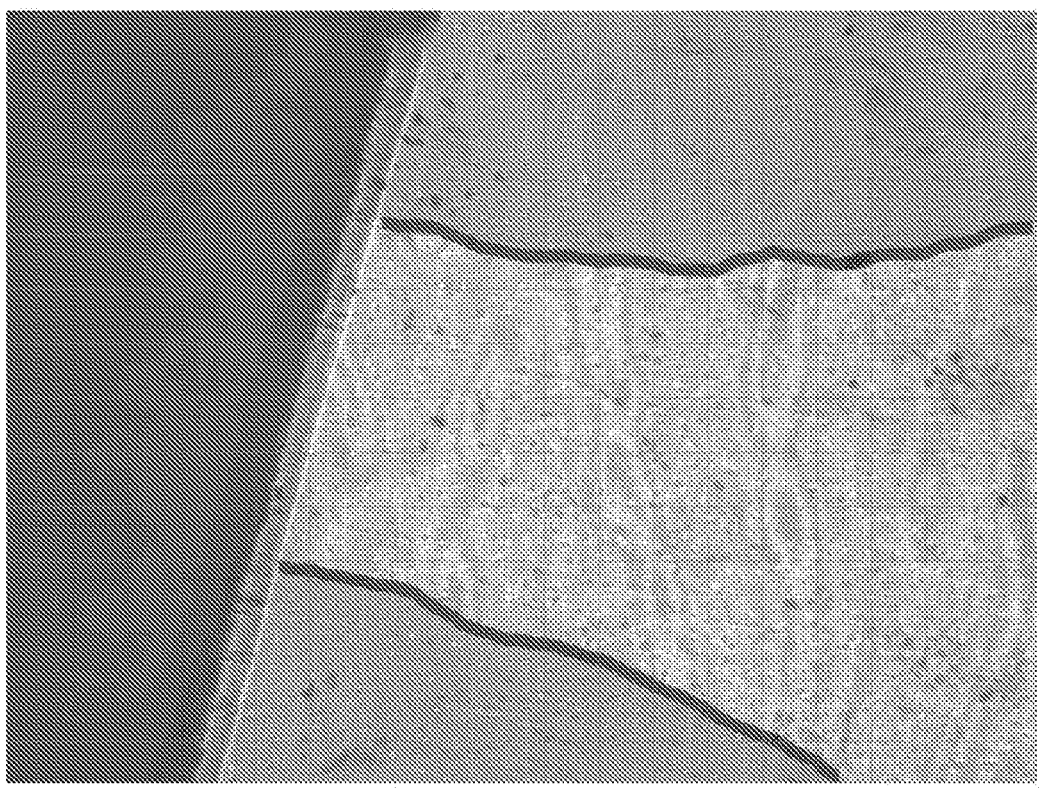

The microscope picture in FIG. 8 shows a dressing where the edge has not been closed properly. Again, the black line is drawn to show the transition between adhesive and no adhesive.

Figure 9:
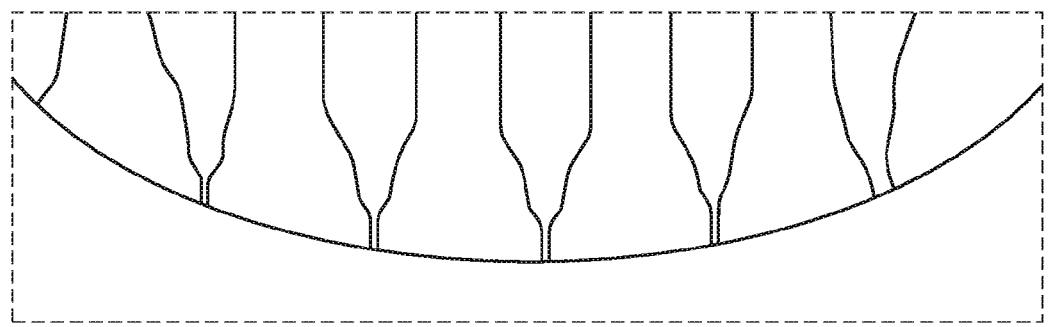

FIG. 9 shows that the edges were open.

Lanes not Defined Properly

Figure 10:
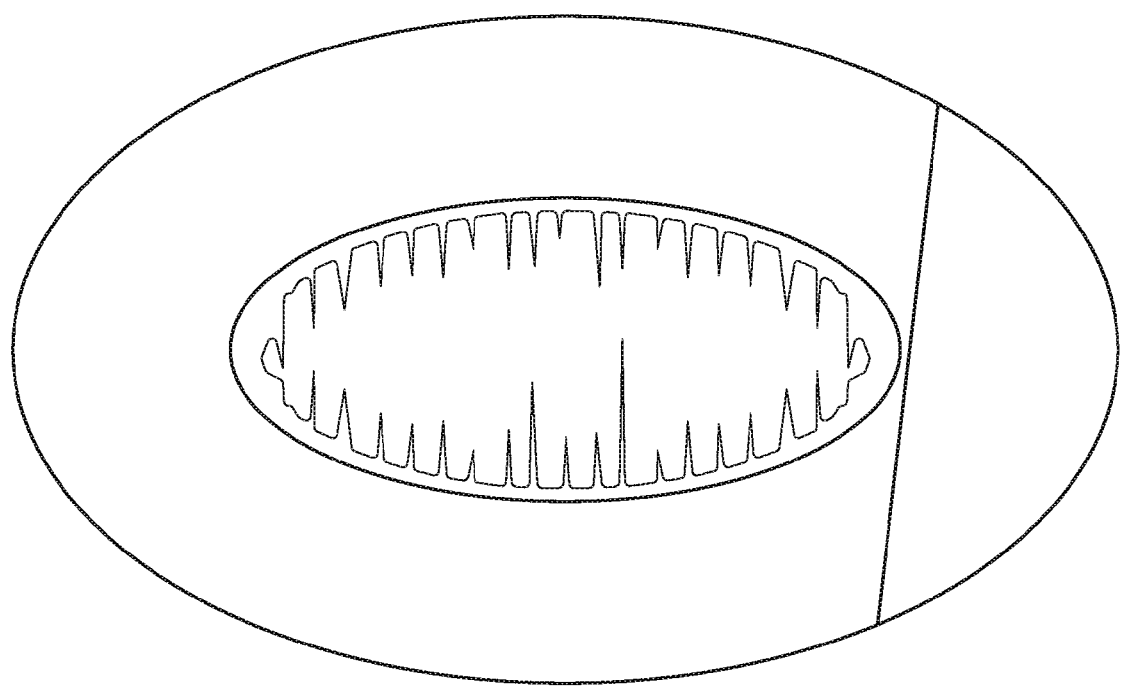

FIG. 10 shows a dressing where the lanes are not well defined, as they flow together, but the edge is closed.

The invention claimed is:

1. An adhesive dressing for application to skin, the adhesive dressing comprising:
a backing layer; and
adhesive placed on the backing layer, the adhesive having
a plurality of discrete lanes of adhesive including a first discrete lane of adhesive applied to the backing layer that is spaced a first distance away from and separated from a second discrete lane of adhesive applied to the backing layer, with the backing layer having no adhesive between each of the plurality of discrete lanes of adhesive;

wherein the first distance between the first discrete lane of adhesive and the second discrete lane of adhesive is less than or equal to a thickness of the first discrete lane of adhesive applied to the backing layer;

wherein the first distance between the first discrete lane of adhesive and the second discrete lane of adhesive is less than or equal to a width of the first discrete lane of adhesive applied to the backing layer.

2. The adhesive dressing of claim 1, wherein the first discrete lane of adhesive is parallel to the second discrete lane of adhesive.

3. The adhesive dressing of claim 1, wherein each of the plurality of discrete lanes of adhesive is rectangular cross-section.

4. The adhesive dressing of claim 1, wherein the second discrete lane of adhesive applied to the backing layer is spaced a second distance away from and separated from a third discrete lane of adhesive applied to the backing layer, and the first distance is equal to the second distance.

5. The adhesive dressing of claim 1, wherein the second discrete lane of adhesive applied to the backing layer is spaced a second distance away from and separated from a third discrete lane of adhesive applied to the backing layer, and the first distance is not equal to the second distance.

6. The adhesive dressing of claim 1, wherein the adhesive dressing has opposed edges located at a perimeter of the adhesive dressing and the first discrete lane of adhesive and the second discrete lane of adhesive extend between the opposed edges of the adhesive dressing.

7. The adhesive dressing of claim 1, wherein the first discrete lane of adhesive and the second discrete lane of adhesive are both linear.

8. The adhesive dressing of claim 1, wherein the adhesive dressing includes a continuous adhesive edge portion deposited on a perimeter of the adhesive dressing.

9. The adhesive dressing of claim 1, wherein the adhesive is a hydrocolloid adhesive.

10. The adhesive dressing of claim 1, wherein the backing layer is water impervious and vapor permeable.

11. The adhesive dressing of claim 1, wherein the backing layer is oriented on a central axis and the plurality of discrete lanes of adhesive is placed on the backing layer at an angle of 45 degrees relative to the central axis.

12. The adhesive dressing of claim 1, wherein the backing layer is one of a transparent material and a translucent material configured to allow the skin to be inspected through the adhesive dressing without loosening the adhesive or removing the adhesive dressing.

* * * * *